(12) United States Patent
Matsumoto (10) Patent No.: US 11,871,906 B2
(45) Date of Patent: Jan. 16, 2024

(54) ENDOSCOPE SYSTEM

(71) Applicant: OLYMPUS CORPORATION, Tokyo (JP)

(72) Inventor: Koji Matsumoto, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 614 days.

(21) Appl. No.: 17/108,205

(22) Filed: Dec. 1, 2020

(65) Prior Publication Data
US 2021/0106207 A1    Apr. 15, 2021

Related U.S. Application Data

(63) Continuation of application No. PCT/JP2018/021590, filed on Jun. 5, 2018.

(51) Int. Cl.
*A61B 1/06* (2006.01)
*A61B 1/00* (2006.01)

(52) U.S. Cl.
CPC ........ *A61B 1/0638* (2013.01); *A61B 1/00006* (2013.01); *A61B 1/000094* (2022.02); *A61B 1/0605* (2022.02)

(58) Field of Classification Search
CPC .......... A61B 1/00006; A61B 1/000094; A61B 1/0605; A61B 1/0638
See application file for complete search history.

(56) References Cited

U.S. PATENT DOCUMENTS

| 6,464,633 B1 | 10/2002 | Hosoda et al. |
| 7,519,096 B2 | 4/2009 | Bouma et al. |
| 8,570,625 B2 | 10/2013 | Kempe et al. |

(Continued)

FOREIGN PATENT DOCUMENTS

| EP | 2229870 A1 | 9/2010 |
| EP | 2520214 A1 | 11/2012 |

(Continued)

OTHER PUBLICATIONS

U.S. Office Action dated Oct. 4, 2021 in U.S. Appl. No. 16/702,839.

(Continued)

*Primary Examiner* — Aaron B Fairchild
(74) *Attorney, Agent, or Firm* — Scully, Scott, Murphy & Presser, P.C.

(57) ABSTRACT

An endoscope system includes: an illumination portion that includes a light source and that is configured to radiate an illumination light beam having a spatially nonuniform intensity distribution onto an imaging subject; a first imager and a second imager disposed at positions that are different from each other and configured to respectively acquire a first illumination image and a second illumination image of the imaging subject being illuminated with the illumination light beam; and at least one processor configured to: create a first deep-layer image and a first surface-layer image from the first illumination image and create a second deep-layer image and a second surface-layer image from the second illumination image; and create a combined deep-layer image by combining the first deep-layer image and the second deep-layer image on the basis of pixel values of the first and second surface-layer images.

6 Claims, 9 Drawing Sheets

(56) References Cited

U.S. PATENT DOCUMENTS

| | | | |
|---|---|---|---|
| 10,251,530 B2 | 4/2019 | Henley et al. | |
| 10,342,459 B2 | 7/2019 | Yokota | |
| 10,972,675 B2* | 4/2021 | Shinji | A61B 1/000094 |
| 11,045,081 B2* | 6/2021 | Matsumoto | A61B 1/07 |
| 11,070,739 B2 | 7/2021 | Matsumoto et al. | |
| 2002/0165456 A1 | 11/2002 | Canpolat et al. | |
| 2008/0192128 A1 | 8/2008 | Kempe et al. | |
| 2008/0252945 A1 | 10/2008 | Kempe et al. | |
| 2009/0058999 A1 | 3/2009 | Gono et al. | |
| 2010/0048995 A1 | 2/2010 | Suijver et al. | |
| 2010/0137682 A1* | 6/2010 | Doguchi | A61B 1/0684 |
| | | | 600/168 |
| 2010/0195078 A1 | 8/2010 | Horiuchi et al. | |
| 2010/0224796 A1 | 9/2010 | Mertz et al. | |
| 2010/0240953 A1 | 9/2010 | Murakami | |
| 2010/0245551 A1 | 9/2010 | Morita | |
| 2011/0263955 A1 | 10/2011 | Narita et al. | |
| 2012/0123205 A1 | 5/2012 | Nie et al. | |
| 2012/0302847 A1 | 11/2012 | Ozawa et al. | |
| 2012/0327205 A1 | 12/2012 | Takahashi | |
| 2013/0270421 A1 | 10/2013 | Kanamori et al. | |
| 2014/0052005 A1 | 2/2014 | Yokota | |
| 2014/0092227 A1 | 4/2014 | Kanamori et al. | |
| 2014/0267657 A1 | 9/2014 | Takei et al. | |
| 2014/0288365 A1 | 9/2014 | Henley et al. | |
| 2014/0316283 A1 | 10/2014 | Kaku et al. | |
| 2015/0022647 A1 | 1/2015 | Takei et al. | |
| 2015/0238089 A1 | 8/2015 | Fujinuma et al. | |
| 2015/0320296 A1* | 11/2015 | Morita | G06T 7/246 |
| | | | 348/65 |
| 2016/0041334 A1 | 2/2016 | Suijver et al. | |
| 2016/0278678 A1 | 9/2016 | Valdes et al. | |
| 2016/0334340 A1 | 11/2016 | Ollivier et al. | |
| 2017/0006202 A1 | 1/2017 | Otani et al. | |
| 2017/0098301 A1 | 4/2017 | Ikemoto et al. | |
| 2017/0143237 A1 | 5/2017 | Yokota | |
| 2017/0231480 A1 | 8/2017 | Yamazaki | |
| 2018/0164221 A1 | 6/2018 | Singh et al. | |
| 2019/0133416 A1 | 5/2019 | Henley et al. | |
| 2019/0274591 A1 | 9/2019 | Yokota | |
| 2020/0099844 A1 | 3/2020 | Shinji et al. | |
| 2020/0099845 A1 | 3/2020 | Matsumoto et al. | |
| 2020/0100650 A1 | 4/2020 | Oka | |
| 2020/0100660 A1 | 4/2020 | Matsumoto et al. | |

FOREIGN PATENT DOCUMENTS

| | | | |
|---|---|---|---|
| EP | 2526854 A1 | 11/2012 | |
| EP | 2979607 A1 | 2/2016 | |
| EP | 3075301 A1 | 10/2016 | |
| EP | 3202306 A1 | 8/2017 | |
| JP | 2009-536066 A | 10/2009 | |
| JP | 2010-213992 A | 9/2010 | |
| JP | 2010-227256 A | 10/2010 | |
| JP | 2012-239816 A | 12/2012 | |
| JP | 2014-18439 A | 2/2014 | |
| JP | 2014-188222 A | 10/2014 | |
| JP | 2015-077415 A | 4/2015 | |
| JP | 2015-231498 A | 12/2015 | |
| JP | 2016-49370 A | 4/2016 | |
| JP | 2016-174836 A | 10/2016 | |
| JP | 2016-198304 A | 12/2016 | |
| JP | 2016-200418 A | 12/2016 | |
| JP | 2016-209466 A | 12/2016 | |
| JP | 2017-042629 A | 3/2017 | |
| WO | 2007/030741 A2 | 3/2007 | |
| WO | 2007/132378 A2 | 11/2007 | |
| WO | 2011/080996 A1 | 7/2011 | |
| WO | 2011/081141 A1 | 7/2011 | |
| WO | 2014/144986 A1 | 9/2014 | |
| WO | 2015/016013 A1 | 2/2015 | |
| WO | 2016/151903 A1 | 9/2016 | |
| WO | 2016/181720 A1 | 11/2016 | |
| WO | 2018/229831 A1 | 12/2018 | |
| WO | 2018/229832 A1 | 12/2018 | |
| WO | 2018/229833 A1 | 12/2018 | |
| WO | 2018/229834 A1 | 12/2018 | |
| WO | 2019/234831 A1 | 12/2019 | |

OTHER PUBLICATIONS

Nayar et al. "Fast Separation of Direct and Global Components of a Scene using High Frequency Illumination." Cited in the ISR for PCT/JP2018/021590 dated Jul. 24, 2018; PCT/JP2018/021597 dated Jul. 24, 2018; PCT/JP2017/021664 dated Aug. 15, 2017; PCT/JP2017/021661 dated Aug. 22, 2017; PCT/JP2017/021665 dated Aug. 22, 2017; and PCT/JP2017/021667 dated Aug. 22, 2017. Published Jul. 2006. pp. 935-944. vol. 25, Issue 3.

Takatani et al. "Decomposition of Reflected and Scattered Lights by Multiple Weighted Measurements." 14th Symposium on Image Recognition and Understanding. Jul. 2011. 14 pages.

Tanaka et al. "Adaptive Frequency Selection under Parallel High-frequency Illumination." 16th Symposium on Image Recognition and Understanding (MIRU2013), Collection of Extended Abstract, Information Processing Society of Japan, Yoshiki Shimotsuma, SS2-33. Cited in the ISR for PCT/JP2017/021661 dated Aug. 22, 2017 and PCT/JP2017/021665 dated Aug. 22, 2017. Jul. 22, 2013. 7 pages.

Takatani et al. "Decomposition of Reflected and Scattered Lights by Multiple Weighted Measurements.", IPSJ SIG Technical Report (CD-ROM), Rombunno. CVIM-177, No. 12, ISSN 2186-2583. vol. 2011, No. 1. Cited in the ISR for PCT/JP2017/021661 dated Aug. 22, 2017 and PCT/JP2017/021665 dated Aug. 22, 2017. Jun. 15, 2011. 13 pages.

U.S. Appl. No. 17/108,216, filed Dec. 1, 2020.

International Search Report dated Aug. 22, 2017, issued in PCT/JP2017/021661, 26 pages.

International Search Report dated Aug. 15, 2017, issued in PCT/JP2017/021664, 14 pages.

International Search Report dated Aug. 22, 2017, issued in PCT/JP2017/021665, 16 pages.

International Search Report dated Aug. 22, 2017, issued in PCT/JP2017/021667, 14 pages.

International Search Report dated Jul. 24, 2018, issued in PCT/JP2018/021590, 23 pages.

International Search Report dated Jul. 24, 2018, issued in PCT/JP2018/021597, 11 pages.

Office Action dated Jun. 19, 2020 received in U.S. Appl. No. 16/691,865, 16 pages.

Office Action dated Dec. 11, 2020 received in U.S. Appl. No. 16/691,961, 11 pages.

Office Action dated Dec. 3, 2020 received in U.S. Appl. No. 16/702,964, 13 pages.

* cited by examiner

ENDOSCOPE SYSTEM

CROSS-REFERENCE TO RELATED APPLICATIONS

This is a continuation of International Application PCT/JP2018/021590 which is hereby incorporated by reference herein in its entirety.

TECHNICAL FIELD

The present invention relates to an endoscope system.

BACKGROUND ART

Light emitted from an illuminated object includes a plurality of components such as specular reflected light, diffuse reflected light, and scattered light. There is a proposed technology that separates object surface information and interior information from each other by separating such components contained in an object image by means of a high-frequency pattern projection method employing structured illumination light having a stripe light-dark pattern (for example, see Non Patent Literature 1).

Structured illumination light is also used in object-shape measurement technologies (for example, see Patent Literatures 1 and 2). In Patent Literature 1, structured illumination light is generated by utilizing light interference, and, in Patent Literature 2, structured illumination light is generated by projecting a lattice pattern formed on a substrate.

CITATION LIST

Non Patent Literature

{NPL 1} TAKATANI Tsuyoshi, et al. "Decomposition of Reflected and Scattered Light by Multiple Weighted Measurements", The 14th Meeting on Image Recognition and Understanding (MIRU2011), July 2011

PATENT LITERATURE

{PTL 1} Japanese Unexamined Patent Application, Publication No. 2016-200418
{PTL 2} Japanese Unexamined Patent Application, Publication No. 2016-198304

SUMMARY OF INVENTION

An aspect of the present invention is an endoscope system including: an illumination portion that includes a light source and that is configured to radiate an illumination light beam onto an imaging subject, the illumination light beam having a spatially nonuniform intensity distribution that contains light portions and dark portions in a beam cross section perpendicular to an optical axis; a first imager configured to acquire a first illumination image of the imaging subject being illuminated with the illumination light beam; a second imager configured to acquire a second illumination image of the imaging subject being illuminated with the illumination light beam and disposed at a different position from the first imager; and at least one processor including hardware, the processor being configured to: create a first deep-layer image and a first surface-layer image from the first illumination image and create a second deep-layer image and a second surface-layer image from the second illumination image, the first deep-layer image containing a greater quantity of information about a deep-layer region of the imaging subject than the first surface-layer image does, and the second deep-layer image containing a greater quantity of information about the deep-layer region of the imaging subject than the second surface-layer image does; and create a combined deep-layer image by combining the first deep-layer image and the second deep-layer image on the basis of pixel values of the first surface-layer image and pixel values of the second surface-layer image.

Another aspect of the present invention is an endoscope system including: a first illumination portion that includes a first light source and that is configured to radiate a first illumination light beam onto an imaging subject, the first illumination light beam having a spatially nonuniform intensity distribution that contains light portions and dark portions in a beam cross section perpendicular to an optical axis; a second illumination portion that includes a second light source, that is configured to radiate a second illumination light beam onto the imaging subject, and that is disposed at a different position from the first illumination portion, the second illumination light beam having a spatially nonuniform intensity distribution that contains light portions and dark portions in a beam cross section perpendicular to an optical axis; an imager configured to acquire a first illumination image of the imaging subject being illuminated with the first illumination light beam and a second illumination image of the imaging subject being illuminated with the second illumination light beam; and at least one processor including hardware, the processor being configured to: create a first deep-layer image and a first surface-layer image from the first illumination image and create a second deep-layer image and a second surface-layer image from the second illumination image, the first deep-layer image containing a greater quantity of information about a deep-layer region of the imaging subject than the first surface-layer image does, and the second deep-layer image containing a greater quantity of information about the deep-layer region of the imaging subject than the second surface-layer image does; and create a combined deep-layer image by combining the first deep-layer image and the second deep-layer image on the basis of pixel values of the first surface-layer image and pixel values of the second surface-layer image.

DESCRIPTION OF EMBODIMENTS

First Embodiment

An endoscope system according to a first embodiment of the present invention will be described with reference to the drawings.

Figure 1:
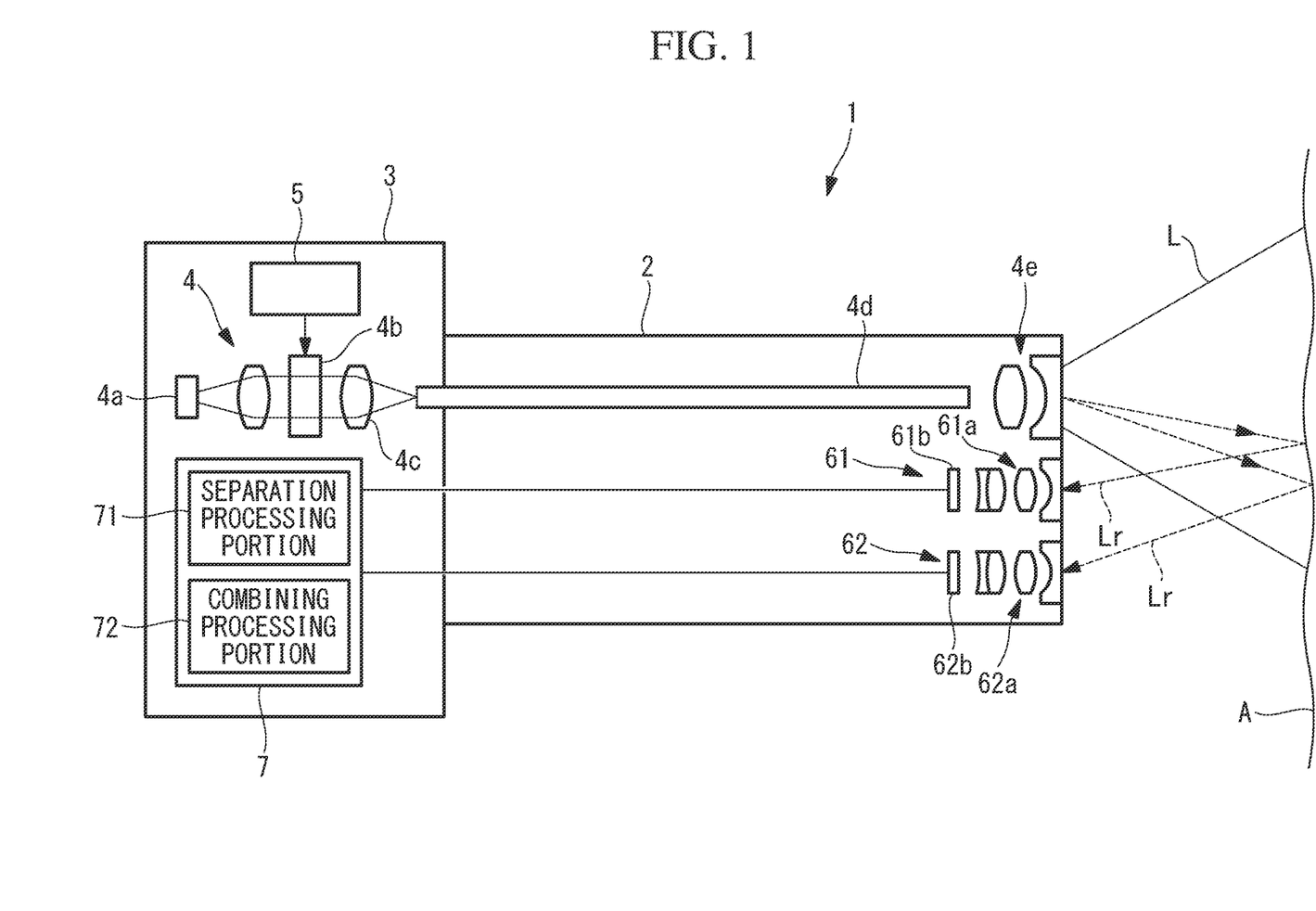
FIG. 1 is an overall configuration diagram of an endoscope system according to a first embodiment of the present invention.

As shown in FIG. 1, an endoscope system 1 according to this embodiment includes an endoscope 2 with which the interior of a body is observed and a main body portion 3 that is connected to a proximal end of the endoscope 2.

In addition, the endoscope system 1 includes: an illumination portion 4 that emits an illumination light beam L having a light-dark pattern toward biological tissue (imaging subject) A in the body from a distal end of the endoscope 2; an intensity-distribution changing portion 5 that causes the light-dark pattern of the illumination light beam L to change over time; two image acquisition portions 61 and 62 that acquire illumination images of the biological tissue A being illuminated with the illumination light beam L; and an image processing portion 7 that creates, from the illumination images, a surface-layer image and a deep-layer image that have information about depths inside the biological tissue A that are different from each other.

Figure 2:
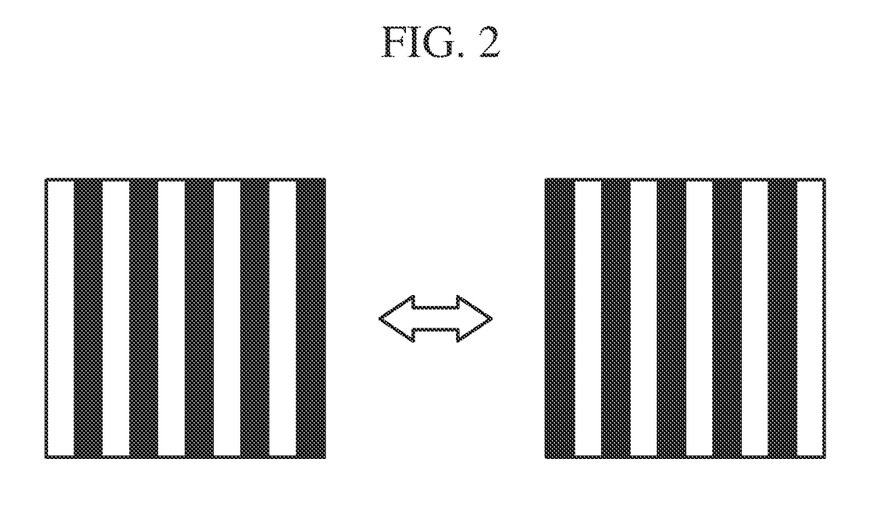
FIG. 2 is a diagram showing an example of the change over time in a light-dark pattern of an illumination light beam.

The illumination portion 4 generates the illumination light beam L, which has a spatially nonuniform intensity distribution in a beam cross section perpendicular to the optical axis, and emits the illumination light beam L toward the biological tissue A. The illumination light beam L is, for example, single-wavelength light such as white light or infrared light, monochromatic light such as red light, green light, and blue light, or mixed light of a plurality of light beams having different wavelengths. In general, the illumination light beam L has an intensity gradient in which the brightness thereof gradually decreases toward the periphery from the center of the beam. Apart from the overall intensity gradient of such a beam cross section, the illumination light beam L has a light-dark pattern in which light portions having high intensities and dark portions having lower intensities than the light portions are repeated in an alternating manner in the beam cross section, as shown in FIG. 2. In FIG. 2, open regions represent the light portions and filled regions represent dark portions.

The illumination portion 4 includes a light source 4a, a mask 4b, and a focusing lens 4c that are provided in the main body portion 3. In addition, the illumination portion 4 includes an image guide fiber 4d and a projection lens 4e that are provided in the endoscope 2.

The light source 4a is, for example, a semiconductor light source such as an LED or an LD. Alternatively, the light source 4a may be an emission end of an optical fiber connected to an external light source device (not shown) of the main body portion 3.

The mask 4b is a liquid crystal element that is capable of electrically controlling light transmittances at respective positions in an entry region at which the light coming from the light source 4a enters, and is constituted of light transmitting regions that allow the light to pass therethrough and light blocking regions that block the light, and thus, a projection pattern corresponding to the light-dark pattern is formed. The light output from the light source 4a has the light-dark pattern imparted thereto as a result of passing through the mask 4b, thus generating the illumination light beam L. Because it is necessary to decrease the size of a starting point of a distal-end portion on an imaging-subject side of the endoscope 2, the generated illumination light beam L is focused by the focusing lens 4c at an entrance end of the image guide fiber 4d, is guided by the image guide fiber 4d while preserving the light-dark pattern until reaching the projection lens 4e provided at the distal end of the endoscope 2, and is emitted from the projection lens 4e in the form of a divergent beam.

The intensity-distribution changing portion 5 is a control element that controls the light transmittances at the respective positions in the entry region of the mask 4b. The intensity-distribution changing portion 5 causes the intensity distribution of the illumination light beam L to change over time so that the light portions and the dark portions are alternated in the beam cross section, as shown in FIG. 2. Accordingly, the light portions and the dark portions are sequentially projected at the respective positions in an area irradiated with the illumination light beam L on a surface B of the biological tissue A.

The first image acquisition portion 61 and the second image acquisition portion 62 are disposed at positions that are different from each other.

The first image acquisition portion 61 includes: an image acquisition lens 61a that is provided at the distal end of the endoscope 2 and that collects the light coming from the biological tissue A; and an image acquisition element 61b that captures an image of the biological tissue A formed by the image acquisition lens 61a. The first image acquisition portion 61 acquires, by means of the image acquisition element 61b, two first illumination images of the biological tissue A illuminated with the illumination light beam L. The two first illumination images are transmitted to the image processing portion 7 from the image acquisition element 61b.

The second image acquisition portion 62 includes: an image acquisition lens 62a that is provided at the distal end of the endoscope 2 and that collects the light coming from the biological tissue A; and an image acquisition element 62b that captures an image of the biological tissue A formed by the image acquisition lens 62a. The second image acquisition portion 62 acquires, by means of the image acquisition element 62b, two second illumination images of the biological tissue A illuminated with the illumination light beam L. The two second illumination images are transmitted to the image processing portion 7 from the image acquisition element 62b.

Figure 3:
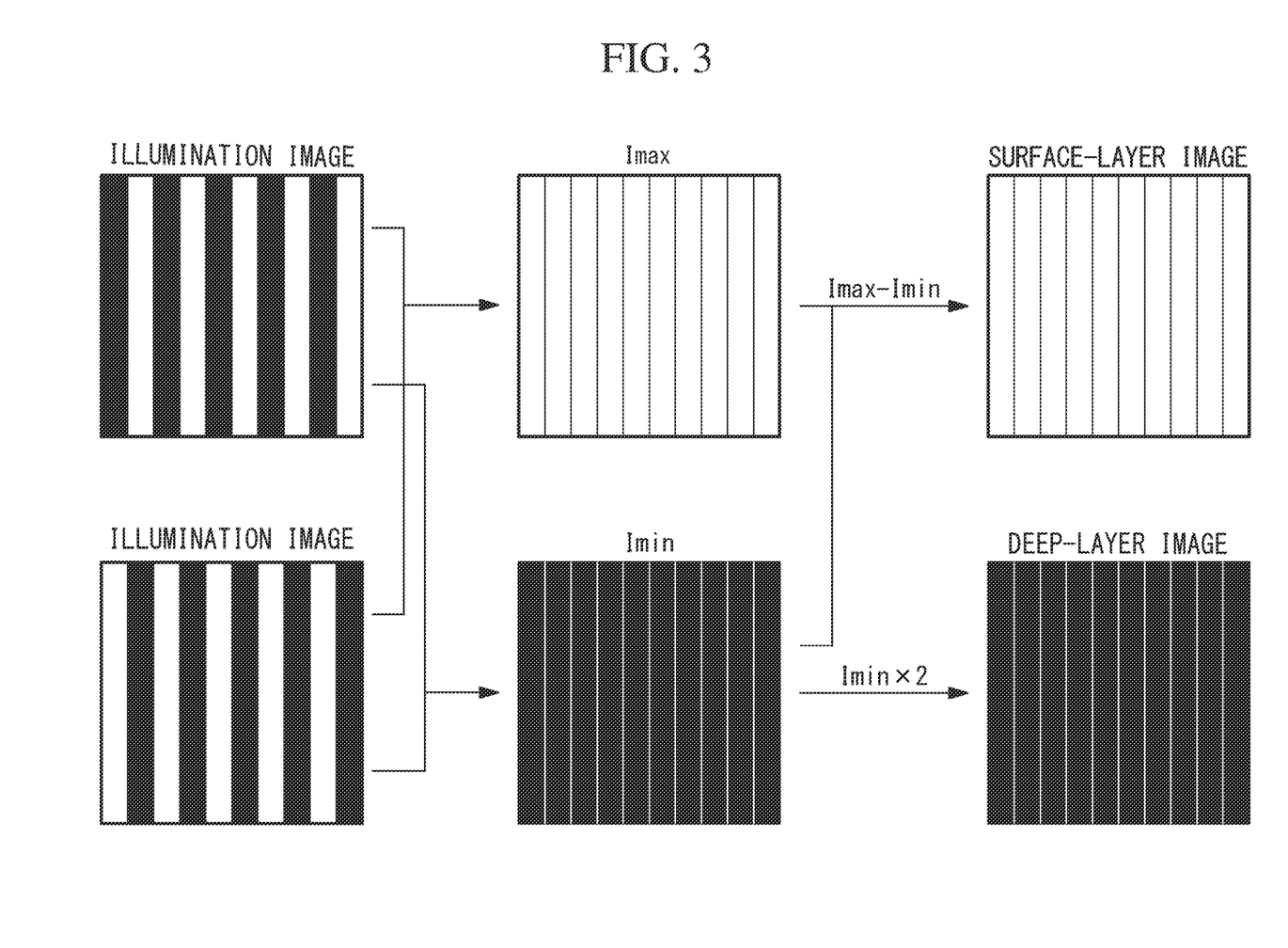
FIG. 3 is a diagram for explaining a method for creating a surface-layer image and a deep-layer image by means of a separation processing portion.

Here, the intensity distribution of the illumination light beam L radiated onto the biological tissue A is changed over time by means of the intensity-distribution changing portion 5, as shown in FIG. 2. The image acquisition element 61b acquires the two first illumination images by executing image capturing at two times at which the biological tissue A is irradiated with the illumination light beam L in which the light portions and the dark portions are inverted with respect to each other, as shown in FIG. 3. The two first illumination images are images in which projection regions of the light portions and projection regions of the dark portions are inverted with respect to each other and in which the projection regions of the light portions are complementary with respect to each other and the projection regions of the dark portions are complementary with respect to each other. In the first illumination images in FIG. 3, open regions represent the projection regions of the light portions and filled regions represent the projection regions of the dark portions. Similarly, the image acquisition element 62b acquires the two second illumination images by executing image capturing at two times at which the biological tissue A is irradiated with the illumination light beam L in which the light portions and the dark portions are inverted with respect to each other. Therefore, the operation of the intensity-distribution changing portion 5 and those of the image acquisition elements 61b and 62b are controlled by a controller (not shown) so that the timing at which the intensity distribution is changed by means of the intensity-distribution changing portion 5 and the timing at which the image acquisition elements 61b and 62b capture images are synchronized with each other.

Figure 4:
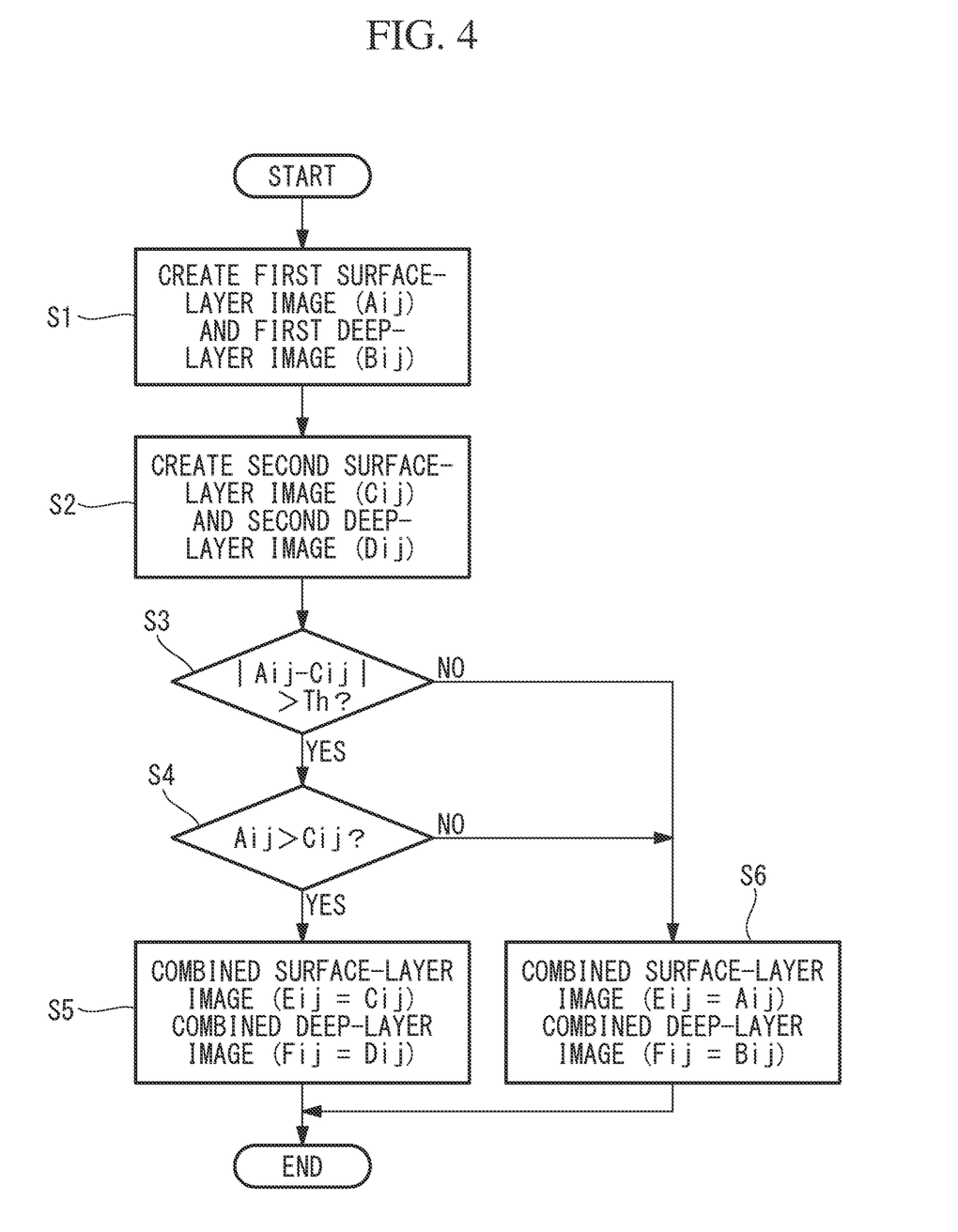
FIG. 4 is a flowchart showing image processing performed by an image processing portion of the endoscope system in FIG. 1.

The image processing portion 7 includes, as functions thereof, a separation processing portion 71 and a combining processing portion 72. FIG. 4 shows processing performed by the image processing portion 7.

As shown in FIG. 3, the separation processing portion 71 creates a first surface-layer image and a first deep-layer image from the two first illumination images (step S1). Regarding pixels at the respective positions in the two first illumination images, intensity values Imax for when the light portions are projected and intensity values Imin for when the dark portions are projected are acquired. The separation processing portion 71 calculates intensity values Is of the respective pixels of the first surface-layer image from Expression (1) below and creates a surface-layer image having the intensity values Is. In addition, the separation processing portion 71 calculates intensity values Id of the respective pixels of the first deep-layer image from Expression (2) below and creates a deep-layer image having the intensity values Id.

$$Is = I\mathrm{max} - I\mathrm{min} \quad (1)$$

$$Id = I\mathrm{min} \times 2 \quad (2)$$

Similarly, the separation processing portion 71 creates a second surface-layer image and a second deep-layer image from the two second illumination images (step S2).

Figure 5:
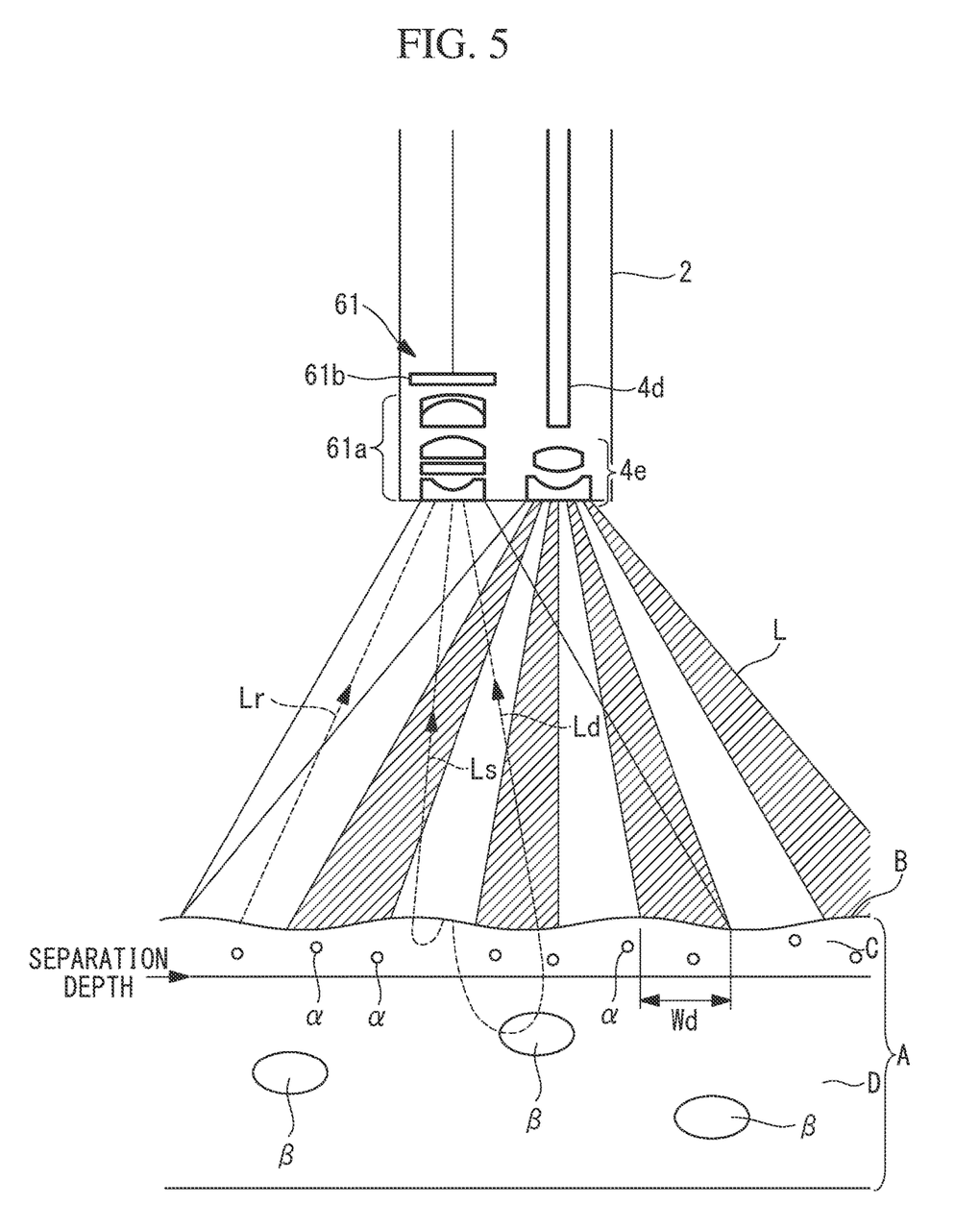
FIG. 5 is a diagram for explaining the relationship between a specular light beam, a surface scattered light beam, and an interior scattered light beam that are generated in biological tissue due to irradiation with the illumination light beam and the positions at which said light beams are generated.

As shown in FIG. 5, when the illumination light beam L having the light-dark pattern is radiated onto the biological tissue A, which is a scatterer, specular reflected light beams (specular light beams) Lr, surface scattered light beams Ls, and interior scattered light beams Ld are generated in the biological tissue A. Reference signs α and β indicate structures present in the biological tissue A, such as blood vessels.

The specular light beams Lr are reflected light generated by specular reflection of the illumination light beam L at the surface B of the biological tissue A and are generated in the projection regions of the light portions.

The surface scattered light beams Ls are scattered light beams generated as a result of the illumination light beam L entering the biological tissue A from the projection regions of the light portions, passing through a surface layer C while repeatedly scattering, and being emitted from the surface B. Most of the surface scattered light beams are emitted from the projection regions of the light portions.

The interior scattered light beams Ld are scattered light beams generated as a result of the illumination light beam L entering the biological tissue A from the projection regions of the light portions, passing through a deep layer D while repeatedly scattering, and being emitted from the surface B. Some of the interior scattered light beams are emitted from the projection regions of the light portions, and other interior scattered light beams are propagated to the projection regions of the dark portions and are emitted from the projection regions of the dark portions.

In other words, the intensity values Imin of the projection regions of the dark portions in the first and second illumination images are mainly based on the interior scattered light beams Ld and mainly contain information about the deep layer D. Therefore, the first and second deep-layer images based on the intensity values Imin are images that mainly contain the information about the deep layer D. On the other hand, the intensity values Imax of the projection regions of the light portions in the first and second illumination images are based on the specular light beams Lr, the surface scattered light beams Ls, and the interior scattered light beams Ld and contain information about the surface B, the surface layer C, and the deep layer D. Therefore, the first and second surface-layer images based on the intensity values Is are images from which the information about the deep layer D is removed and that mainly contain the information about the surface B and the surface layer C.

Here, the image acquisition lens 61a of the first image acquisition portion 61 and the image acquisition lens 62a of the second image acquisition portion 62 are disposed at the positions that are different from each other on a distal-end surface of the endoscope 2. Because of this, the specular light beams Lr generated at certain positions on the surface B of the biological tissue A wound not enter both of the first image acquisition portion 61 and the second image acquisition portion 62. Therefore, the positions of the specular light beams Lr in the first illumination images and the positions of the specular light beams Lr in the second illumination images are different from each other, and, as shown in FIG. 6, the positions of the specular light beams Lr in the first surface-layer image and the positions of the specular light beams Lr in the second surface-layer image are also different from each other.

In the case in which the contrast of the illumination light beam L between the light portions and the dark portions is low and the intensities of the dark portions are not sufficiently low, the specular light beams Lr are also generated in the projection regions of the dark portions in some cases. Information about the specular light beams Lr generated in the projection regions of the dark portions is separated into the deep-layer image. Therefore, as shown in FIG. 6, high-luminance noise N based on the specular light beams Lr appears in the deep-layer image in some cases. The positions of the noise N in the first deep-layer image are the same as the positions of the specular light beams Lr in the first surface-layer image, and the positions of the noise N in the second deep-layer image are the same as the positions of the specular light beams Lr in the second surface-layer image.

Figure 6:
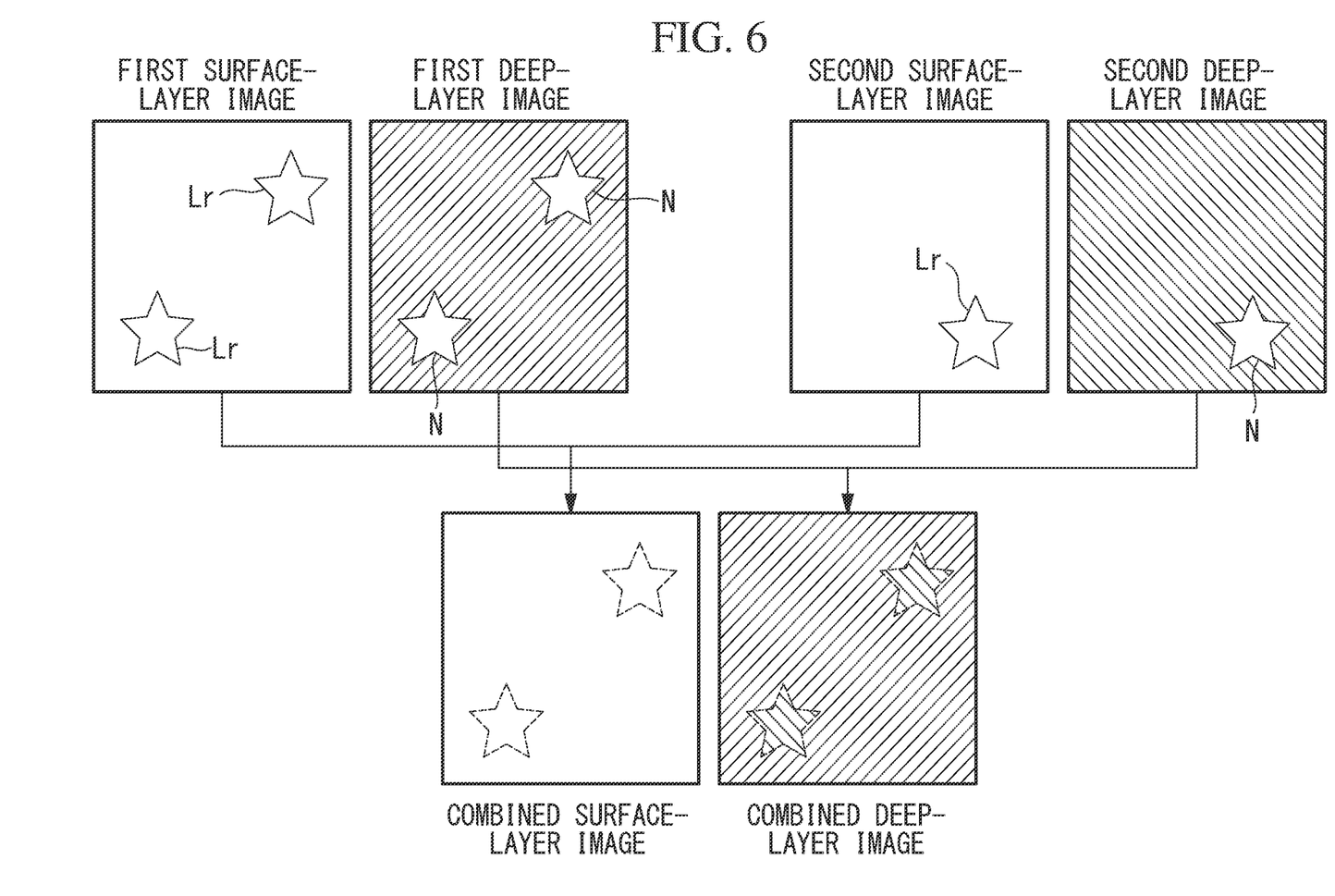
FIG. 6 is a diagram for explaining a method for creating a combined surface-layer image and a combined deep-layer image by means of a combining processing portion.

As shown in FIG. 6, the combining processing portion 72 creates a combined surface-layer image in which the first surface-layer image and the second surface-layer image are combined. In addition, the combining processing portion 72 creates a combined deep-layer image in which the first deep-layer image and the second deep-layer image are combined.

As shown in FIG. 4, first, the combining processing portion 72 detects the specular light beams Lr in the first surface-layer image and the noise N in the first deep-layer image on the basis of differences in the pixel values of the first surface-layer image and the second surface-layer image (steps S3 and S4). The surface-layer image contains a greater quantity of information about the specular light beams Lr as compared with the deep-layer image. Therefore, it is possible to accurately detect the specular light beams Lr on the basis of the pixel values of the first and second surface-layer images.

Specifically, the combining processing portion 72 calculates absolute values |Aij−Cij| of differences between pixel values Aij and Cij of corresponding pixels ij in the first surface-layer image and the second surface-layer image and compares the absolute values |Aij−Cij| with a prescribed threshold Th (step S3). As described above, the positions of the specular light beams Lr are different between the first surface-layer image and the second surface-layer image. Therefore, the absolute values |Aij−Cij| of the differences between the pixel values Aij of the first surface-layer image and the pixel values Cij of the second surface-layer image become greater than the prescribed threshold Th at the positions of the specular light beams Lr.

In the case in which the absolute values are equal to or less than the prescribed threshold Th ("NO" in step S3), the combining processing portion 72 determines that the specular light beams Lr are not occurring at the positions of the pixels ij, and selects the pixel values Aij of the first surface-layer image and the pixel values Bij of the first deep-layer image as pixel values Eij of the combined surface-layer image and pixel values Fij of the combined deep-layer image, respectively (step S6).

On the other hand, in the case in which the absolute values |Aij−Cij| are greater than the prescribed threshold Th ("YES" in step S3), the combining processing portion 72 determines in which one of the first surface-layer image and the second surface-layer image the specular light beams Lr are occurring by comparing the pixel values Aij and the pixel values Cij (step S4).

In the case in which the specular light beams Lr are occurring in the first surface-layer image, the pixel values Aij become greater than the pixel values Cij. In the case in which the pixel values Aij are greater than the pixel values Cij ("YES" in step S4), the combining processing portion 72 selects the pixel values Cij of the second surface-layer image as the pixel values Eij of the combined surface-layer image and selects the pixel values Dij of the second deep-layer image as the pixel values Fij of the combined deep-layer image (step S5).

On the other hand, in the case in which the specular light beams Lr are occurring in the second surface-layer image, the pixel values Aij become less than the pixel values Cij. In the case in which the pixel values Aij are less than the pixel values Cij ("NO" in step S4), the combining processing portion 72 selects the pixel values Aij of the first surface-layer image as the pixel values Eij of the combined surface-layer image and selects the pixel values Bij of the first deep-layer image as the pixel values Fij of the combined deep-layer image (step S6).

Through the above steps S4-S6, the regions of the specular light beams Lr are removed from the first surface-layer image, and regions corresponding to the regions of the specular light beams Lr in the first surface-layer image are selected from the second surface-layer image. Then, the combined surface-layer image is created by combining the regions selected from the second surface-layer image with the first surface-layer image from which the regions of the specular light beams Lr have been removed. In addition, the regions of the noise N are removed from the first deep-layer image, and regions corresponding to the regions of the noise N in the first deep-layer image are selected from the second deep-layer image. Then, the combined deep-layer image is created by combining the regions selected from the second deep-layer image with the first deep-layer image from which the regions of the noise N have been removed.

As has been described above, with this embodiment, the first illumination images and the second illumination images in which the positions of the specular light beams Lr are different from each other are acquired as a result of acquiring, by means of the two image acquisition portions 61 and 62 that are disposed at the positions that are different from each other, the images of the biological tissue A being illuminated with the illumination light beam L coming from the shared illumination portion 4. Then, the first deep-layer image and the second deep-layer image in which the positions of the noise N based on the specular light beams Lr are different from each other are created from the first and second illumination images. In addition, the first and second surface-layer images that respectively contain the specular light beams Lr at the same positions as the noise N in the first and second deep-layer images are created from the first and second illumination images.

Accordingly, the noise N that occurs in the first and second deep-layer images in the case in which the contrast of the high-frequency pattern of the illumination light beam L is low is accurately detected on the basis of the pixel values of the first and second surface-layer images, and thus, there is an advantage in that it is possible to create, from the first and second deep-layer images, the combined deep-layer image from which the noise N has been removed.

Figure 7A:
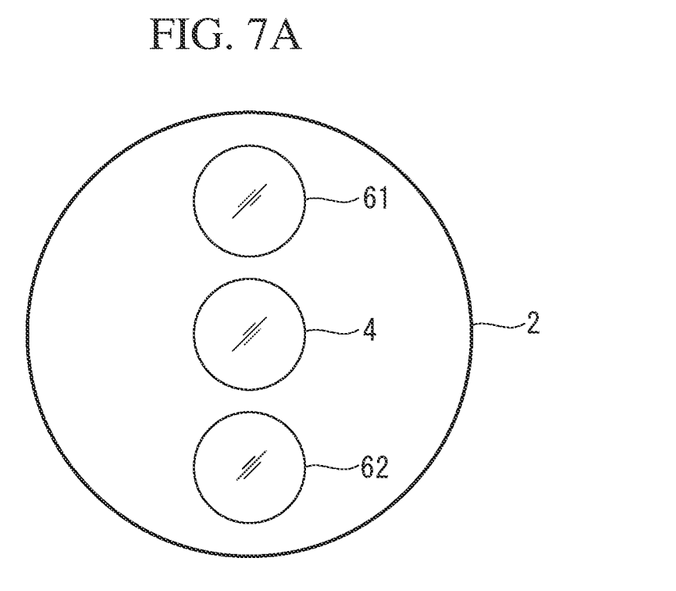
FIG. 7A is a diagram showing another example of a manner in which an illumination portion and two image acquisition portions are disposed when a distal-end surface of an endoscope is viewed from the front side.

FIG. 7A shows another example of the manner in which the illumination portion 4 and the image acquisition portions 61 and 62 are disposed at the distal-end surface of the endoscope 2. As shown in FIG. 7A, the first image acquisition portion 61 and the second image acquisition portion 62 may be disposed on either side of the illumination portion 4. In addition, the distance between the first image acquisition portion 61 and the illumination portion 4 and the distance between the second image acquisition portion 62 and the illumination portion 4 may be different from each other. As a result of making the distances and the directions of the first image acquisition portion 61 and the second image acquisition portion 62 with respect to the illumination portion 4 differ from each other, it is possible to reliably make the positions of the specular light beams Lr and the noise N differ between the first surface-layer image and the second surface-layer image and between the first deep-layer image and the second deep-layer image.

Figure 7B:
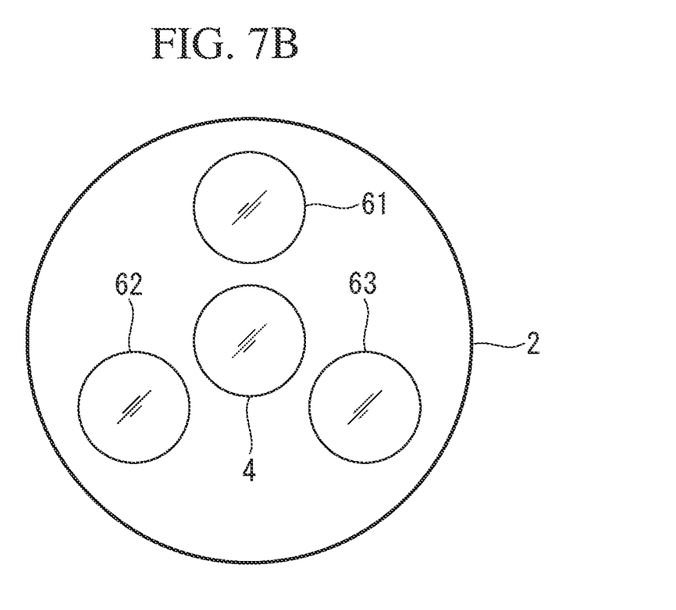
FIG. 7B is a diagram showing an example of a manner in which the illumination portion and three image acquisition portions are disposed when the distal-end surface of the endoscope is viewed from the front side.

This embodiment is provided with the two image acquisition portions 61 and 62; however, alternatively, three or more image acquisition portions may be provided. FIG. 7B shows an example of the manner in which the illumination portion 4 and three image acquisition portions 61, 62, and 63 are disposed at the distal-end surface of the endoscope 2. As shown in FIG. 7B, as a result of making the distances and the directions of the three image acquisition portions 61, 62, and 63 with respect to the illumination portion 4 differ from each other, it is possible to reliably acquire illumination images in which the specular light beam Lr does not occur at any position in any one of the illumination images, and it is possible to reliably create a combined deep-layer image that does not contain the noise N.

Second Embodiment

Next, an endoscope system according to a second embodiment of the present invention will be described with reference to the drawings.

In this embodiment, configurations that are different from those of the first embodiment will be described, and configurations that are the same as those of the first embodiment will be given the same reference signs and the descriptions thereof will be omitted.

Figure 8:
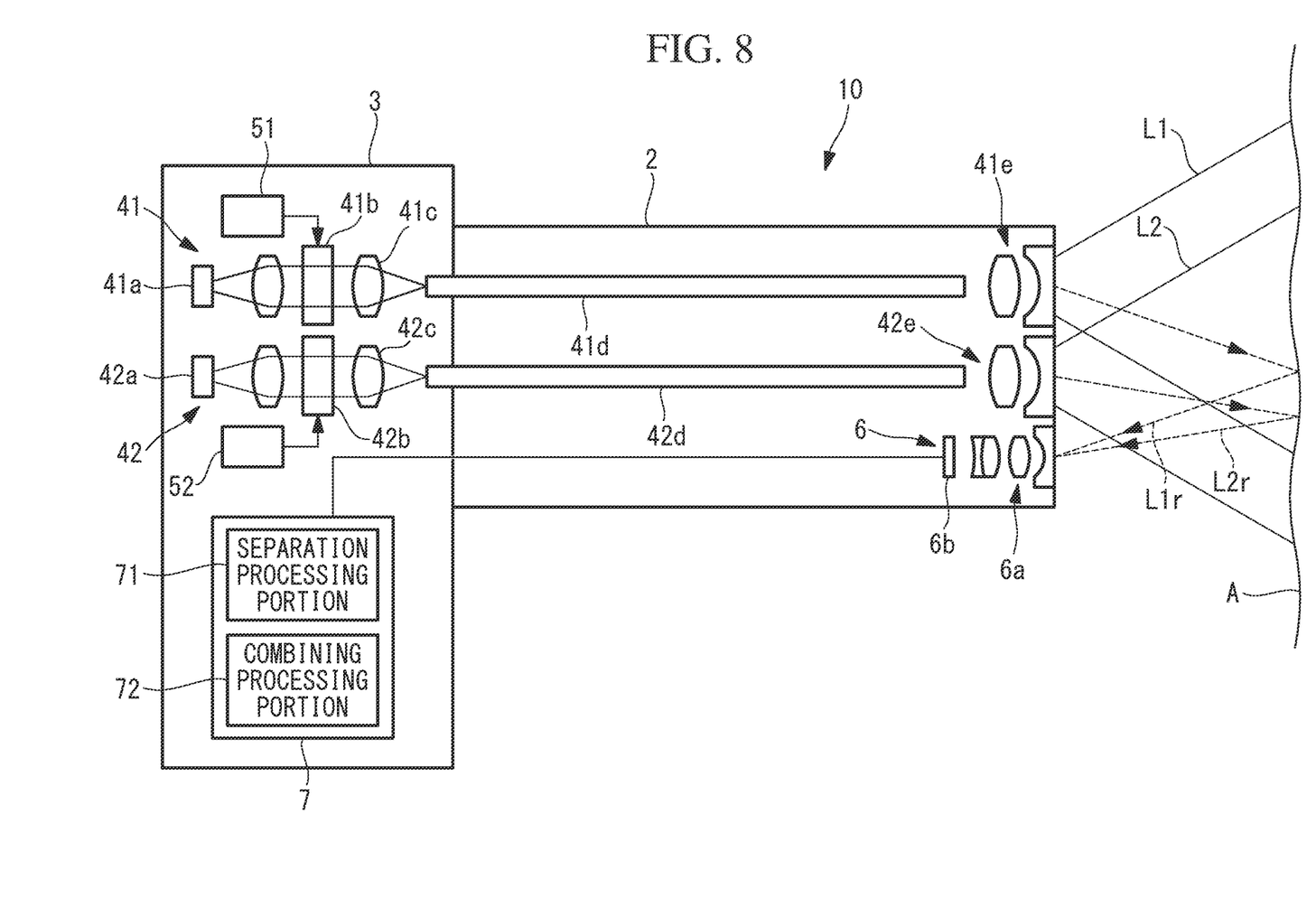
FIG. 8 is an overall configuration diagram of an endoscope system according to a second embodiment of the present invention.

As shown in FIG. 8, an endoscope system 10 according to this embodiment includes the endoscope 2 and the main body portion 3. In addition, the endoscope system 10 includes: two illumination portions 41 and 42 that respectively emit illumination light beams L1 and L2 toward the biological tissue (imaging subject) A in the body from the distal end of the endoscope 2; intensity-distribution changing portions 51 and 52; an image acquisition portion 6 that acquires an illumination image of the biological tissue A being illuminated with the illumination light beams L; and the image processing portion 7.

The first illumination portion 41 and the second illumination portion 42 are disposed at positions that are different from each other. The first illumination portion 41 includes a light source 41a, a mask 41b, a focusing lens 41c, an image guide fiber 41d, and a projection lens 41e. The second illumination portion 42 includes a light source 42a, a mask 42b, a focusing lens 42c, an image guide fiber 42d, and a projection lens 42e. The light sources 41a and 42a, the masks 41b and 42b, the focusing lenses 41c and 42c, the image guide fibers 41d and 42d, and the projection lenses 41e and 42e are configured in the same manner as the light source 4a, the mask 4b, the focusing lens 4c, the image guide fiber 4d, and the projection lens 4e, respectively. The first illumination portion 41 generates the first illumination light beam L1 and radiates the first illumination light beam L1 onto the biological tissue A. The second illumination portion 42 generates the second illumination light beam L2 and radiates the second illumination light beam L2 onto the biological tissue A. The first and second illumination light beams L1 and L2 are the same as the illumination light beam L. The first illumination portion 41 and the second illumination portion 42 radiate the illumination light beams L1 and L2 onto the biological tissue A in a time division manner.

The first intensity-distribution changing portion 51 is a control element that controls the mask 41b and causes the light-dark pattern of the first illumination light beam L1 to change over time.

The second intensity-distribution changing portion 52 is a control element that controls the mask 42b and causes the light-dark pattern of the second illumination light beam L2 to change over time.

The image acquisition portion 6 includes an image acquisition lens 6a and an image acquisition element 6b. The image acquisition lens 6a and the image acquisition element 6b are configured in the same manner as the image acquisition lens 61a and the image acquisition element 61b, respectively. The image acquisition portion 6 acquires, by means of the image acquisition element 6b, two first illumination images of the biological tissue A being illuminated with the first illumination light beam L1 and acquires, by means of the image acquisition element 6b, two second illumination images of the biological tissue A being illuminated with the second illumination light beam L2. The two first illumination images and the two second illumination images are transmitted to the image processing portion 7 from the image acquisition element 6b. Therefore, the operations of the illumination portions 41 and 42, the intensity-distribution changing portions 51 and 52, and the image acquisition element 6b are controlled by the controller so that the timing at which the illumination light beams L1 and L2 are emitted from the illumination portions 41 and 42, the timing at which the intensity distributions are changed by means of the intensity-distribution changing portions 51 and 52, and the timing at which the image acquisition element 6b captures the images are synchronized.

Here, the first illumination portion 41 and the second illumination portion 42 are disposed at positions that are different from each other. Therefore, specular light beams L1r of the first illumination light beam L1 and specular light beams L2r of the second illumination light beam L2 that are generated at the same positions on the surface B of the biological tissue A do not enter the shared image acquisition portion 6. Therefore, as with the first embodiment, the positions of the specular light beams Lr in the first illumination images and the positions of the specular light beams Lr in the second illumination images are different from each other.

As with the first embodiment, the separation processing portion 71 creates a first surface-layer image and a first deep-layer image from the two first illumination images and creates a second surface-layer image and a second deep-layer image from the two second illumination images.

As with the first embodiment, the combining processing portion 72 creates a combined surface-layer image from the first surface-layer image and the second surface-layer image and creates a combined deep-layer image from the first deep-layer image and the second deep-layer image.

As has been described above, with this embodiment, the first illumination images and the second illumination images in which the positions of the specular light beams Lr are different from each other are acquired as a result of acquiring, by means of the shared image acquisition portion 6, the images of the biological tissue A being illuminated with the illumination light beams L1 and L2 coming from the two illumination portions 41 and 42 that are disposed at the positions that are different from each other. Therefore, as with the first embodiment, noise N that occurs in the first and second deep-layer images in the case in which the contrasts of the high-frequency patterns of the illumination light beams L are low is accurately detected on the basis of the pixel values of the first and second surface-layer images, and thus, there is an advantage in that it is possible to create, from the first and second deep-layer images, the combined deep-layer image from which the noise N has been removed.

Figure 9A:
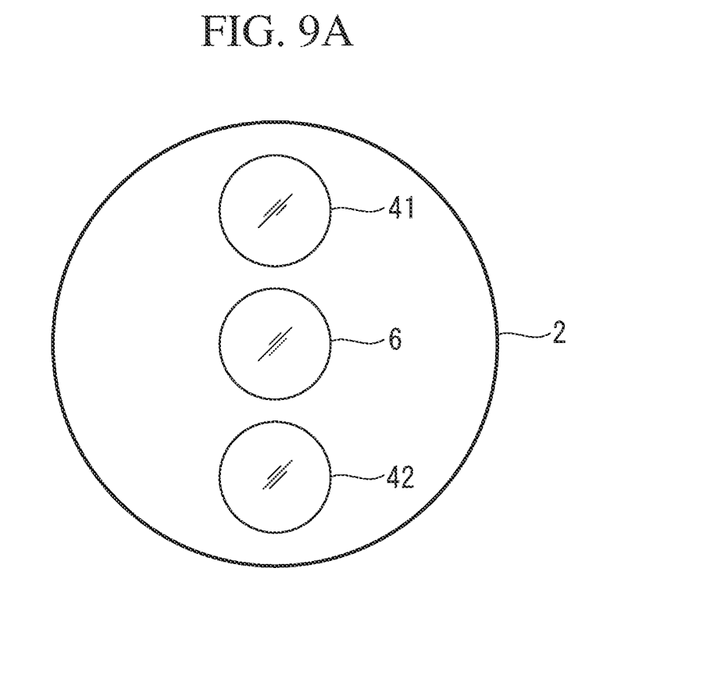
FIG. 9A is a diagram showing another example of a manner in which two illumination portions and an image acquisition portion are disposed when the distal-end of the endoscope is viewed from the front side.

FIG. 9A shows another example of the manner in which the illumination portions 41 and 42 and the image acquisition portion 6 are disposed at the distal-end surface of the endoscope 2. As shown in FIG. 9A, the first illumination portion 41 and the second illumination portion 42 may be disposed on either side of the image acquisition portion 6. In addition, the distance between the first illumination portion 41 and the image acquisition portion 6 and the distance between the second illumination portion 42 and the image acquisition portion 6 may be different from each other. As a result of making the distances and the directions of the first illumination portion 41 and the second illumination portion 42 with respect to the image acquisition portion 6 differ from each other in this way, it is possible to reliably make the positions of the specular light beams Lr and the noise N differ between the first surface-layer image and the second surface-layer image and between the first deep-layer image and the second deep-layer image.

Figure 9B:
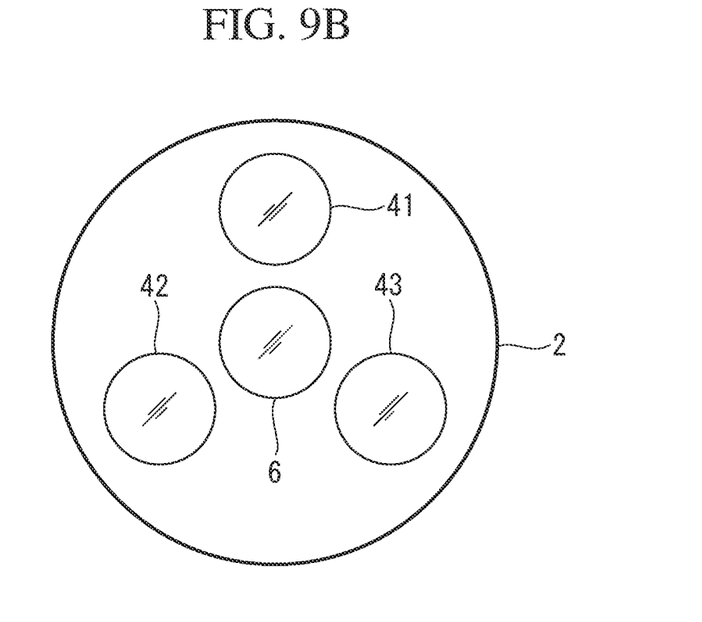
FIG. 9B is a diagram showing an example of a manner in which three illumination portions and the image acquisition portion are disposed when the distal-end surface of the endoscope is viewed from the front side.

This embodiment is provided with the two illumination portions 41 and 42; however, alternatively, three or more illumination portions may be provided. FIG. 9B shows an example of a manner in which the three illumination portions 41, 42, and 43 and the image acquisition portion 6 are disposed at the distal-end surface of the endoscope 2. As shown in FIG. 9B, as a result of making the distances and the directions of the three illumination portions 41, 42, and 43 with respect to the image acquisition portion 6 differ from each other, it is possible to reliably acquire illumination images in which the specular light beam Lr does not occur at any position in any one of the illumination images, and it is possible to reliably create a combined deep-layer image that does not contain the noise N.

In the first and second embodiments, the illumination portion 4, 41, 42 illuminates the biological tissue A with the illumination light beam L, L1, L2 having a stripe-like intensity distribution; however, the intensity distribution pattern of the illumination light beam L, L1, L2 is not limited thereto, and other distributions in which the light portions and the dark portions are spatially repeated may be employed. For example, the intensity distribution of the illumination light beam L, L1, L2 may be a checkered pattern, dots, or random dots.

In the first and the second embodiments, the illumination portion 4, 41, 42 generates the illumination light beam L, L1, L2 having a light-dark pattern by means of the liquid crystal element 4b, 41b, 42b, and the intensity-distribution changing portion 5, 51, 52 causes the light-dark pattern to change by controlling the liquid crystal element 4b, 41b, 42b; however, the configurations of the illumination portion 4, 41, 42 and the intensity-distribution changing portion 5, 51, 52 are not limited thereto.

For example, the illumination portion 4, 41, 42 may utilize interference fringes of the two laser light beams as the light-dark pattern, and the intensity-distribution changing portion 5, 51, 52 may shift the positions of the interference fringes in a direction orthogonal to the optical axis of the illumination light beam by changing the optical-path length of one of the two laser light beams.

Alternatively, the illumination portion 4, 41, 42 may form a light-dark pattern on the surface B of the biological tissue A in a shadow-picture-like manner by causing light to pass through a mask in which a projection pattern corresponding to the light-dark pattern is formed. In this case, the intensity-distribution changing portion 5, 51, 52 causes the intensity distributions to change over time by relatively moving the mask and the light emitting portion that emits the light toward the mask in the width directions of the light portions and the dark portions.

In the first and second embodiments, the intensity-distribution changing portion 5, 51, 52 may cause the intensity distribution of the illumination light beam L, L1, L2 to continuously change between two light-dark patterns in which the light portions and the dark portions are inverted with respect to each other.

In the case in which the light-dark patterns are continuously changed, the image acquisition portion 61, 62, 6 may acquire three or more illumination images in which the positions of the projection regions of the light portions and the projection regions of the dark portions are different from each other by executing the image capturing at three or more times at which the positions of the light portions and the dark portions are different from each other. The separation processing portion 71 may create a surface-layer image and a deep-layer image from the three or more illumination images. In this case, because three or more intensity values are obtained with respect to pixels at the respective positions, the intensity values Is and Id are calculated by using a maximum intensity value as Imax and a minimum intensity value as Imin.

In the first and second embodiments, it is preferable that the illumination portion 4, 41, 42 emit the illumination light beam L, L1, L2, which is a divergent beam, toward the biological tissue A so that the light-dark pattern projected on the surface B of the biological tissue A expands in a proportional manner with respect to the image-capturing distance between the biological tissue A and the image acquisition portion 61, 62, 6.

As shown in FIG. 5, a separation depth between a surface-layer image and a deep-layer image depends on widths Wd of the dark portions on the surface B of the biological tissue A. The separation depth is an approximate boundary between the depth of the information contained in a surface-layer image and the depth of the information contained in a deep-layer image. With an increase in the widths Wd of the dark portions, the separation depth increases, and a deep-layer image in which information about a deeper position is emphasized is obtained. Therefore, it is possible to acquire deep-layer images in which information about different depths is emphasized by expanding and contracting the light-dark pattern on the surface B of the biological tissue A by changing the image-capturing distance.

The first and second embodiments may additionally include an image-capturing-distance measuring portion that measures an image-capturing distance between the biological tissue A and the image acquisition portion 6, 61, 62, and the intensity-distribution changing portion 5, 51, 52 may adjust the spatial periods between the light portions and the dark portions in the light-dark pattern on the basis of the imaging-capturing distance so that the spatial periods between the light portions and the dark portions on the surface B of the biological tissue A are kept constant independently of the image-capturing distance.

By employing such a configuration, it is possible to create a combined deep-layer image containing the information about a prescribed depth independently of the image-capturing distance.

As the image-capturing-distance measuring portion, it is possible to employ a publicly known arbitrary means that is capable of measuring the image-capturing distance without coming into contact with the biological tissue A.

In the first and second embodiments, the illumination portion 4, 41, 42 may illuminate the biological tissue A with the illumination light beam L, L1, L2 consisting of a plurality of light beams having wavelengths that are different from each other. For example, the illumination light beam L, L1, L2 may be a white light beam in which three light beams, that is, red, green, and blue, are mixed.

In the case in which a plurality of light beams having wavelengths that are different from each other are used as the illumination light beam L, L1, L2, the intensity distributions of the respective light beams may be made to differ in accordance with the wavelengths so that the periods of the light portions and the dark portions decrease with an increase in the wavelengths.

In general, light is scattered by a scatterer more strongly as the wavelength decreases. Therefore, it is difficult for a blue light beam to reach the deep layer D of the biological tissue A as compared with a red light beam, and information contained in an interior scattered light beam of a blue light beam becomes information about a shallow position as compared with information about an interior scattered light beam of a red light beam. Therefore, by decreasing the periods of the light portions and the dark portions with an increase in the wavelength, it is possible to control the depths of the information contained in the interior scattered light beams of the respective colors so that interior scattered light beams of all of the red, green, and blue light beams have information about the same depth.

The above-described embodiment also leads to the following aspects.

An aspect of the present invention is an endoscope system including: an illumination portion that radiates an illumination light beam onto an imaging subject, the illumination light beam having a spatially nonuniform intensity distribution that contains light portions and dark portions in a beam cross section perpendicular to an optical axis; a first image acquisition portion that acquires a first illumination image of the imaging subject being illuminated with the illumination light beam; a second image acquisition portion that acquires a second illumination image of the imaging subject being illuminated with the illumination light beam and that is disposed at a different position from the first image acquisition portion; a separation processing portion that creates a first deep-layer image and a first surface-layer image from the first illumination image and that creates a second deep-layer image and a second surface-layer image from the second illumination image, the first deep-layer image containing a greater quantity of information about a deep-layer region of the imaging subject than the first surface-layer image does, and the second deep-layer image containing a greater quantity of information about the deep-layer region of the imaging subject than the second surface-layer image does; and a combining processing portion that creates a combined deep-layer image by combining the first deep-layer image and the second deep-layer image on the basis of pixel values of the first surface-layer image and pixel values of the second surface-layer image.

With this aspect, when the illumination light beam is radiated onto the imaging subject, which is a scatterer, specular reflected light beams (specular light beams), which are generated by specular reflection at the surface of the imaging subject, surface scattered light beams, which are emitted from the surface of the imaging subject after being scattered in the surface layer of the interior of the imaging subject, and interior scattered light beams, which are emitted from the surface of the imaging subject after being scattered in the deep layer in the interior of the imaging subject, are generated. As a result of radiating the illumination light beam, which has a spatially nonuniform intensity distribution, onto the imaging subject from the illumination portion, the interior scattered light beams are spatially separated from the specular light beams and the surface scattered light beams. In other words, the specular light beams, the surface scattered light beams, and the interior scattered light beams are generated in the light portions, whereas the interior scattered light beams, which have been bent to reach the dark portion from the light portion, are predominantly generated in the dark portions.

Therefore, in the illumination images acquired by the image acquisition portion, the regions corresponding to the dark portions contain a large quantity of information about the deep layer, and the regions corresponding to the light portions contain a large quantity of information about the surface and the surface layer. The information refers to, for example, the light level of light that enters the biological tissue and that is emitted from the biological tissue after being subjected to modulation such as scattering or absorption due to the biological tissue and a structure in the interior thereof. The separation processing portion creates, on the basis of the pixel values of the regions corresponding to the dark portions, the deep layer image, which contains a large quantity of information about the deep layer of the imaging subject. In addition, the separation processing portion creates, on the basis of the pixel values of the region corresponding to the light portions, the surface-layer image, which contains a large quantity of information about the surface and the surface layer of the imaging subject.

In the case in which the contrast of the illumination light beam is low, the specular light beams are generated in the regions of the dark portions on the surface of the imaging subject in some cases, and, as a result, high-luminance noise based on the specular light beams occurs in the first deep-layer image and the second deep-layer image in some cases. Because the first image acquisition portion and the second image acquisition portion are disposed at positions that are different from each other, the positions of the noise based on the specular light beams are also different between the first deep-layer image and the second deep-layer image.

The positions of the noise in the first deep-layer image are the same as the positions of the specular light beams in the first surface-layer image. The positions of the noise in the second deep-layer image are the same as the positions of the specular light beams in the second surface-layer image. Therefore, it is possible to combine, by means of the combining processing portion, the first deep-layer image and the second deep-layer image while removing the noise on the basis of the pixel values of the first and second surface-layer images. Accordingly, even in a state in which the contrast of the high-frequency pattern of the illumination light beam is low, it is possible to provide a combined deep-layer image that does not contain noise based on specular light beams.

Another aspect of the present invention is an endoscope system including: a first illumination portion that radiates a first illumination light beam onto an imaging subject, the first illumination light beam having a spatially nonuniform intensity distribution that contains light portions and dark portions in a beam cross section perpendicular to an optical axis; a second illumination portion that radiates a second illumination light beam onto the imaging subject and that is disposed at a different position from the first illumination portion, the second illumination light beam having a spatially nonuniform intensity distribution that contains light portions and dark portions in a beam cross section perpendicular to an optical axis; an image acquisition portion that acquires a first illumination image of the imaging subject being illuminated with the first illumination light beam and a second illumination image of the imaging subject being illuminated with the second illumination light beam; a separation processing portion that creates a first deep-layer image and a first surface-layer image from the first illumination image and that creates a second deep-layer image and a second surface-layer image from the second illumination image, the first deep-layer image containing a greater quantity of information about a deep-layer region of the imaging subject than the first surface-layer image does, and the second deep-layer image containing a greater quantity of information about the deep-layer region of the imaging subject than the second surface-layer image does; and a combining processing portion that creates a combined deep-layer image by combining the first deep-layer image and the second deep-layer image on the basis of pixel values of the first surface-layer image and pixel values of the second surface-layer image.

With this aspect, in the case in which the contrast of the illumination light beam is low, the specular light beams are generated in the regions of the dark portions on the surface of the imaging subject in some cases, and, as a result, high-luminance noise based on the specular light beams occurs in the first deep-layer image and the second deep-layer image in some cases. Because the first illumination portion and the second illumination portion are disposed at the positions that are different from each other, the positions of the noise based on the specular light beams are different between the first deep-layer image and the second deep-layer image.

The positions of the noise in the first deep-layer image are the same as the positions of the specular light beams in the first surface-layer image. The positions of the noise in the second deep-layer image are the same as the positions of the specular light beams in the second surface-layer image. Therefore, it is possible to combine, by means of the combining processing portion, the first deep-layer image and the second deep-layer image while removing the noise on the basis of the pixel values of the first and second surface-layer images. Accordingly, even in a state in which the contrast of the high-frequency pattern of the illumination light beam is low, it is possible to provide a combined deep-layer image that does not contain noise based on specular light beams.

In the above-described aspect, the combining processing portion may create the combined deep-layer image by detecting a noise region based on specular light in the first deep-layer image on the basis of differences between the pixel values of the first surface-layer image and the second surface-layer image and by combining a region in the second deep-layer image corresponding to the detected noise region in the first deep-layer image with the detected noise region in the first deep-layer image.

As described above, the positions of the noise in the first deep-layer image are the same as the positions of the specular light beams in the first surface-layer image, and, at the positions of the specular light beams in the first surface-layer image, the pixel values of the first surface-layer image become considerably greater than the pixel values of the second surface-layer image. Therefore, it is possible to detect the noise regions in the first deep-layer image on the basis of the differences between the pixel values of the first surface-layer image and the second surface-layer image. In addition, it is possible to create a combined deep-layer image from which the noise has been removed by combining corresponding regions in the second deep-layer image with the noise regions in the first deep-layer image.

The above-described aspect may include an intensity-distribution changing portion that changes periods of the light portions and the dark portions in the intensity distribution.

The separation depth between the surface-layer image and the deep-layer image depends on the widths of the dark portions in the imaging subject. The separation depth is an approximate boundary between the depth of the information about the surface layer contained in the surface-layer image and the depth of the information about the deep layer contained in the deep-layer image. As a result of changing the widths of the dark portions in the imaging subject by means of the intensity-distribution changing portion, it is possible to control the separation depth so as to create a deep-layer image in which information about a desired depth is emphasized.

The above-described aspect may include an image-capturing-distance measuring portion that measures an image-capturing distance between the image acquisition portion and the imaging subject, wherein the intensity-distribution changing portion may change the periods of the light portions and the dark portions in the intensity distribution on the basis of the image-capturing distance so that the intensity distribution of the illumination light beam on the imaging subject becomes constant independently of the distance between the image acquisition portion and the imaging subject.

With this configuration, it is possible to create a deep-layer image containing information about a certain depth independently of the image-capturing distance.

In the above-described aspect, the illumination portion may emit the illumination light beam in a form of a divergent beam so that pattern of the light portions and the dark portions on the imaging subject expands in a proportional manner with respect to an image-capturing distance between the image acquisition portion and the imaging subject.

With this configuration, it is possible to change the widths of the dark portions in the imaging subject simply by changing the image-capturing distance.

In the above-described aspect, the illumination light beam may consist of a plurality of light beams having wavelengths that are different from each other, and the plurality of light beams have the intensity distributions in which periods of the light portions and the dark portions decrease with an increase in the wavelengths.

Because the light that has entered the imaging subject reaches a deeper position with an increase in the wavelength thereof, the interior scattered light beams of light having greater wavelengths contain information about deeper layers. It is possible to decrease the differences in the depths of the information due to the differences in the wavelengths by decreasing the periods of the light portions and the dark portions with an increase in the wavelengths.

REFERENCE SIGNS LIST 1, 10 endoscope system
2 endoscope
3 main body portion
4, 41, 42 illumination portion
5, 51, 52 intensity-distribution changing portion
6, 61, 62 image acquisition portion
7 image processing portion
71 separation processing portion
72 combining processing portion
Lr specular light
N noise

The invention claimed is:

1. An endoscope system comprising:
a first illumination portion that comprises a first light source and that is configured to radiate a first illumination light beam onto an imaging subject, the first illumination light beam having a spatially nonuniform intensity distribution that contains light portions and dark portions in a beam cross section perpendicular to an optical axis of the first illumination light beam;
a second illumination portion that comprises a second light source, that is configured to radiate a second illumination light beam onto the imaging subject, and that is disposed at a different position from the first illumination portion, the second illumination light beam having a spatially nonuniform intensity distribution that contains light portions and dark portions in a beam cross section perpendicular to an optical axis of the second illumination light beam;

an imager configured to acquire a first illumination image of the imaging subject being illuminated with the first illumination light beam and a second illumination image of the imaging subject being illuminated with the second illumination light beam; and at least one processor comprising hardware, the processor being configured to:

create a first deep-layer image and a first surface-layer image from the first illumination image and create a second deep-layer image and a second surface-layer image from the second illumination image, the first deep-layer image containing a greater quantity of information about a deep-layer region of the imaging subject than the first surface-layer image does, and the second deep-layer image containing a greater quantity of information about the deep-layer region of the imaging subject than the second surface-layer image does; and create a combined deep-layer image by combining the first deep-layer image and the second deep-layer image on the basis of pixel values of the first surface-layer image and pixel values of the second surface-layer image.

2. The endoscope system according to claim 1, wherein the processor is configured to create the combined deep-layer image by detecting a noise region based on specular light in the first deep-layer image on the basis of differences between the pixel values of the first surface-layer image and the second surface-layer image and by combining a region in the second deep-layer image corresponding to the detected noise region in the first deep-layer image with the detected noise region in the first deep-layer image.

3. The endoscope system according to claim 1, further comprising a controller configured to change periods of the light portions and the dark portions in the intensity distribution of the first and second illumination light beams.

4. The endoscope system according to claim 3, further comprising:

a meter configured to measure an image-capturing distance between the imager and the imaging subject, wherein the controller is configured to change the periods of the light portions and the dark portions in the intensity distribution of the first and second illumination light beams on the basis of the image-capturing distance so that the intensity distribution of the first and second illumination light beams on the imaging subject becomes constant independently of a distance between the imager and the imaging subject.

5. The endoscope system according to claim 1, wherein the illumination portion is configured to emit the first and second illumination light beams in a form of a divergent beam so that pattern of the light portions and the dark portions on the imaging subject expands in a proportional manner with respect to an image-capturing distance between the imager and the imaging subject.

6. The endoscope system according to claim 1, wherein the first and second illumination light beams consist of a plurality of light beams having wavelengths that are different from each other, and the plurality of light beams have the intensity distributions in which periods of the light portions and the dark portions decrease with an increase in the wavelengths.

\* \* \* \* \*